United States Patent
Lebrun

(10) Patent No.: US 10,041,922 B2
(45) Date of Patent: Aug. 7, 2018

(54) BIOCHEMISTRY BASED OCULAR TOXICITY ASSAY

(71) Applicant: Stewart Lebrun, Anaheim, CA (US)

(72) Inventor: Stewart Lebrun, Anaheim, CA (US)

( * ) Notice: Subject to any disclaimer, the term of this patent is extended or adjusted under 35 U.S.C. 154(b) by 387 days.

(21) Appl. No.: 15/087,875

(22) Filed: Mar. 31, 2016

(65) Prior Publication Data

US 2016/0290982 A1 Oct. 6, 2016

Related U.S. Application Data

(60) Provisional application No. 62/140,679, filed on Mar. 31, 2015.

(51) Int. Cl.
*G01N 33/15* (2006.01)
*G01N 33/44* (2006.01)
*G01N 21/25* (2006.01)

(52) U.S. Cl.
CPC .......... *G01N 33/15* (2013.01); *G01N 21/25* (2013.01); *G01N 33/44* (2013.01)

(58) Field of Classification Search
CPC ......... G01N 21/25; G01N 33/15; G01N 33/44
USPC ............. 436/163, 164, 174; 422/68.1, 82.05, 422/82.09
See application file for complete search history.

(56) References Cited

U.S. PATENT DOCUMENTS

| | | | | |
|---|---|---|---|---|
| 4,613,574 A | * | 9/1986 | Bergman | G01N 33/5014 436/164 |
| 6,020,148 A | * | 2/2000 | Osborne | C07D 209/48 435/26 |
| 2013/0115608 A1 | * | 5/2013 | McKim | C12Q 1/025 435/6.12 |

OTHER PUBLICATIONS

Lebrun, Stewart J. Cosmetics and Toiletries, vol. 127, No. 7, Jul. 2012, pp. 498-502.*
Curren et al. Food and Chemical Toxicology, vol. 35, 1997, pp. 127-158.*

* cited by examiner

*Primary Examiner* — Maureen Wallenhorst
(74) *Attorney, Agent, or Firm* — Knobbe Martens Olson & Bear LLP

(57) ABSTRACT

Disclosed are in vitro methods for predicting the relative irritancy of a test substance. The disclosed methods include a first assay for water insoluble test substances and a second assay for water soluble test substances. The combined results of both assays provide greater sensitivity and accuracy in predicting relative irritancy than tests for water soluble irritants alone.

20 Claims, 5 Drawing Sheets

BIOCHEMISTRY BASED OCULAR TOXICITY ASSAY

BACKGROUND

Field

The present disclosure relates to methods and kits for in vitro testing of irritants.

Description of the Related Art

Traditionally, ocular irritation testing has been conducted using rabbits. A test substance is applied to the conjunctival sack of rabbits under restraint for 4 hours, followed by a 14 or 21-day test period. After the first hour and on days 1, 2, 3, 4, 7 and 14 or 21, the immune response—i.e., redness, swelling and discharge, as well as tissue damage, are evaluated in three areas of the eye: the cornea, iris and conjunctiva. One purpose of this test is to evaluate any opacity caused by the test substance in the cornea of the eye and to measure it. Any disruption to the pigmented iris surrounding the pupil, which is deeper within the eye than the cornea, is also measured, and the conjunctiva or tissue surrounding the eye is evaluated for redness, chemosis and discharge.

The extent of damage, at each organ location are evaluated and scored. These scores are used to classify a test substance as either non-irritant, irritant or corrosive. Ocular irritation is distinguished from ocular corrosion based on reversibility. If, after 14 or 21 days, there is still a response, the substance is classified as corrosive but if the effect has reversed, the substance is classified as an irritant. A non-irritant induces little measurable change at each tissue site, whereas an irritant induces swelling and lesions at one or more sites. In addition, diffuse redness and distinct blood vessel damage are evaluated at the conjunctiva. At the cornea, opacity is evaluated. Corrosives induce similar types of damage, but the damage will never fully reverse which may cause scarring or loss of vision.

There are two predominant modern classification systems. The Environmental Protection Agency (EPA) protection system is used predominantly within the United States, while the Globally Harmonized System (GHS) is used predominantly in international commerce. The EPA and GHS classify irritants based on the severity of irritation as depicted Table 1 below.

TABLE 1

| Classification System | No Irritation | Mild Irritation | Moderate Irritation | Severe Irritation (Corrosion) |
|---|---|---|---|---|
| EPA | Category IV | Category III | Category II | Category I |
| GHS | NC (Not Classified) | Category 2 | Category 2 | Category 1 |

Irritation testing is also used to satisfy U.S. FDA and international safety labeling requirements and plays an important role in commercial product liability and consumer product satisfaction. Guidance documents produced by the Organization for Economic Trade and Development (OECD) are available to coordinate international trade. The OECD describes the standard rabbit eye test, which is the primary method for eye safety evaluation, and Safety Data Sheet documentation which accompanies hazardous chemicals and products.

The restraint of the animals as well as the test duration required by traditional methods of ocular irritation testing has raised public concern over unnecessary animal suffering. There is broad-based objection and aggressive lobbying against cosmetic and personal care product testing using animals. The "not tested on animals" label appeals to a large segment of consumers. In addition, US regulators discourage animal testing for ocular irritation, and Europe has banned animal testing for most consumer product labeling. Interestingly, at the same time that animal testing was banned in 2013, Europe also will mandate safety guidance labeling; the United States is expected to follow suit.

There are a limited number of ocular irritation tests that do not require the use of animals. These tests include cell culture-based tests, tests based on excised animal eyes, slugs, egg-based tests, and one other existing biochemical tests that measures a single water soluble variable.

Cell culture-based tests typically involve applying the test substance to a differentiated human tissue grown in a petri dish, to determine its toxicity based on the degree of cells killed by the substance after a fixed time. Tests based on fertilized eggs, or the Hen's Egg Test Chorioallantoic Membrane (HET-CAM), measure changes to the vessels that extend from the developing yolk to the air cell within the egg; this primitive respiratory tissue or chorioallantoic membrane is the CAM. These vessels, present early in development before the egg is considered an animal, can be used to determine the irritancy and corrosivity of a test substance. It has been suggested that the vessels in the CAM are similar to those in the conjunctiva. When the test is conducted, the substance is applied to the CAM and changes to the vessels—typically lysis, coagulation and hemorrhage, are measured and used to predict ocular irritancy and corrosivity.

There remains an unmet need for an accurate cell free test for the assessment of ocular irritation.

SUMMARY

An in vitro method is disclosed for predicting a relative irritancy of a test substance, which is at least partially insoluble in an aqueous solution. The method comprises: adding the test substance to an aliquot of a hydrophobic organic polymer to form a test hydrophobic organic polymer; adding a known irritant to another aliquot of the hydrophobic organic polymer to form a control hydrophobic organic polymer; measuring an optical response of the test and control hydrophobic organic polymers after a time period; and predicting the relative irritancy of the test substance by comparing the measured optical response in the test and control hydrophobic organic polymers.

In a variation, the disclosed in vitro method may further include a solubility pretest for determining if the test substance is at least partially insoluble in an aqueous solution. The solubility pretest includes: adding the test substance to an aqueous solution to form a pretest solution; mixing the pretest solution; and measuring an optical response, wherein an optical response of greater than a predetermined threshold indicates that the test substance is at least partially insoluble in an aqueous solution.

In one embodiment, the step of measuring the optical response includes measuring spectrophotometric changes in optical density, opacity or turbidity.

In a variation, the disclosed in vitro method may further include classifying the test substance as an irritant if the measured optical response produced by the test substance is greater than or equal to the measured optical response produced by the known irritant.

In another variation, the disclosed in vitro method may further include adding a known non-irritant to another aliquot of the hydrophobic organic polymer.

In one embodiment, more than one known irritants and/or known non-irritants are used to generate a standard curve of relative irritancy versus the measured optical response.

In one embodiment, the hydrophobic organic polymer comprises a polymerized hydrocarbon.

In one embodiment, an in vitro method is disclosed for predicting a relative irritancy of a test substance. The method includes: measuring an initial pH of an aqueous solution having one or more macromolecules; adding a test substance to the aqueous solution to form a test solution; monitoring a shift in pH of the test solution from the initial pH to a final pH; adjusting the pH of aliquot of the aqueous solution having one or more macromolecules to the final pH using an acid or a base to form a control solution; adding a known irritant to a first aliquot of the control solution at the final pH; measuring an optical response of the macromolecules in the test solution and the control solution; and predicting the relative irritancy of the test substance by comparing the measured optical response in the test and control solutions.

In a variation, the disclosed in vitro method may further include adding a known non-irritant to a second aliquot of the control solution at the final pH.

In a variation, the disclosed in vitro method may further include classifying the test substance as an irritant if the optical response produced by the test substance is greater than or equal to the optical response produced by the known irritant.

In one embodiment, measuring the optical response includes measuring spectrophotometric changes in optical density, opacity or turbidity.

In one embodiment, more than one known irritants and/or known non-irritants are used to generate a standard curve of relative irritancy versus the measured optical response.

In one embodiment, a background optical response is measured in the aqueous solution having the test substance and/or the known irritant, wherein the one or more macromolecules are not included in the aqueous solution, and wherein the background optical response is subtracted from the measured optical response in the test solution and/or control solution.

In one embodiment, the test substance is partially solubilized with a solvent before adding it to the aqueous solution, and wherein the optical response produced by the solvent in the aqueous solution is subtracted from the optical response produced by the test substance and the solvent.

An in vitro method is disclosed in accordance with another embodiment, where the method includes conducting a first assay for water insoluble irritants, a second assay for water soluble irritants, and combining the results of the first and second assays. The first assay includes: adding the test substance to an aliquot of a hydrophobic organic polymer to form a test hydrophobic organic polymer; adding a known irritant to another aliquot of the hydrophobic organic polymer to form a control hydrophobic organic polymer; measuring an optical response of the test and control hydrophobic organic polymers after a time period; and predicting the relative irritancy of the test substance under hydrophobic conditions by comparing the measured optical response in the test and control hydrophobic organic polymers. The second assay includes: adding the test substance to an aliquot of an aqueous solution having one or more macromolecules to form a test solution; adding a known irritant to another aliquot of the aqueous solution comprising one or more macromolecules to form a control solution; measuring an optical response of the macromolecules in the test solution and the control solution; and predicting the relative irritancy of the test substance under aqueous conditions by comparing the measured optical response in the test and control solutions. The results from the first and second assays are combined to provide the composite predicted relative irritancy.

In a variation, the disclosed in vitro method may further include a solubility pretest for determining if the test substance is at least partially insoluble in water. The solubility pretest includes: adding the test substance to an aqueous solution to form a pretest solution; mixing the pretest solution; and measuring an optical response, where an optical response of greater than a predetermined threshold indicates that the test substance is at least partially insoluble in water.

In one embodiment, measuring the optical response includes measuring spectrophotometric changes in optical density, opacity or turbidity.

In one embodiment, more than one known irritants and/or known non-irritants are used to generate a standard curve of relative irritancy versus the measured optical response.

DETAILED DESCRIPTION

Figure 1:
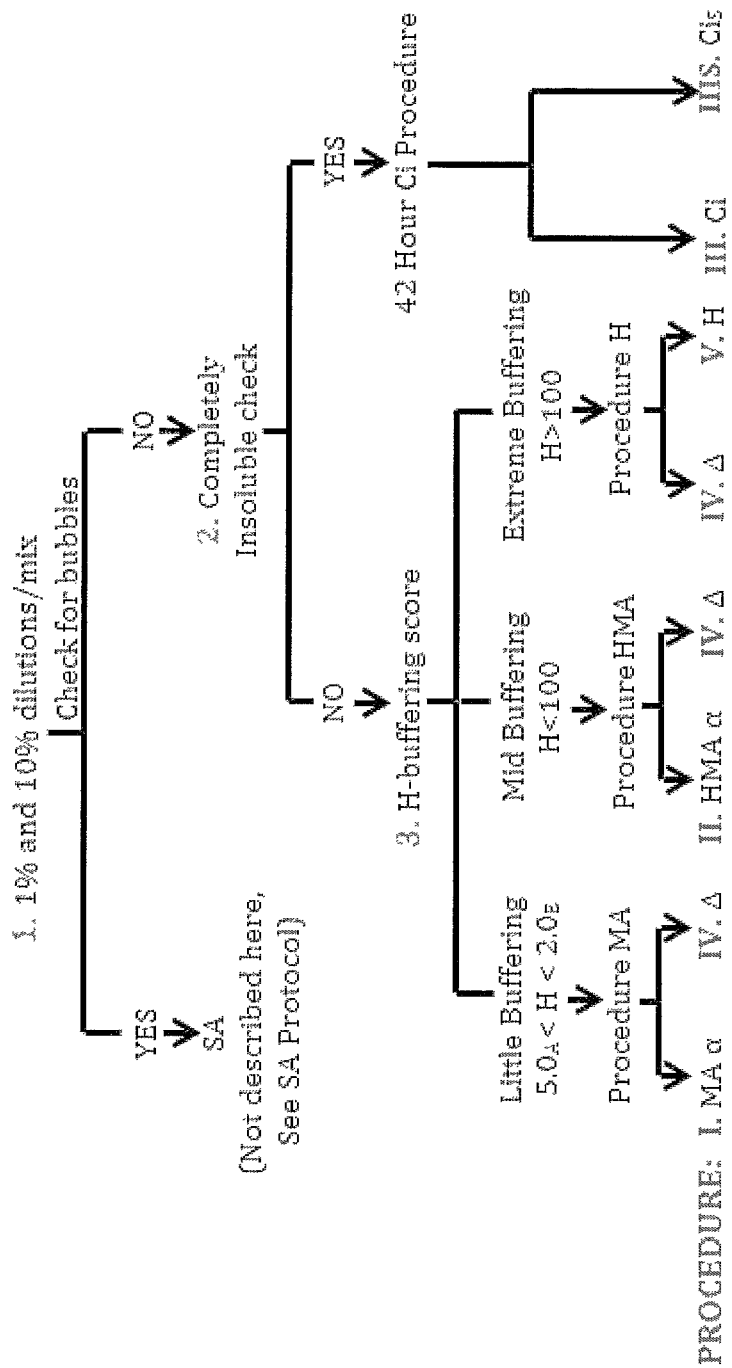
FIG. 1 shows an example testing protocol stemming from an initial pretest.

The assay described herein is the first such assay that controls for the buffering capacity of the test substance and combines both water-soluble and water insoluble sub-assays; consequently, sensitivity and accuracy are substantially improved over existing in vitro tests for potential irritants.

Acids and bases have a profound effect on protein conformation. Protein structure is maintained by hydrogen bonds and charge interactions. Disruption of these interactions results in protein denaturation and complete loss of function. The human cornea is comprised of highly organized collagen. It is organized specifically to allow light transmission and vision. This is arguably, one of the most elegant examples of highly specific protein folding and resultant functionality. Corneal opacity results from ocular collagen denaturation or damage.

Denaturation results from both pH related unfolding and other chemical mechanisms, such as oxidation and reduction. The extent of denaturation can be evaluated by measuring the development of opacity in a protein based test matrix, similar to the manner in which egg white proteins denature and become opaque when heated. The opacity measurement produced by test substances is then compared to a separate set of standards, including known irritants and/or known non-irritants. These standards also induce opacity to the protein based test matrix. When an unknown substance induces an opacity that matches or exceeds the opacity of known irritant standards, the substance is predicted to be an irritant. The pH of the test solution can be modified by the buffering power or capacity of some test substances, and may therefore induce pH-dependent protein denaturation and opacity in the test system. Accordingly, the test system described above provides an indirect measure of pH effects, buffering capacity and acid/alkaline reserve as measured by the change in optical responses of proteins and glycoproteins in the test system. Given the importance of pH effects on protein confirmation, previous development efforts have been directed to measuring the pH of the test substance, consistent with biochemistry and an extension of the use of pH as a measure of the potential to induce tissue corrosion. These previous development efforts have resulted in the Irritection and Eytex assay methods. Unfortunately, measuring the pH of the test substance as a simple metric of potential irritancy fails to address the more important and complex impact of the buffering capacity of the test substance on the final pH of the test system—which is a far more accurate prediction of the pH-dependent irritancy.

Accordingly, the Irritection and Eytex assay methods currently available to avoid in vivo animal testing are not sufficiently accurate. The Mid-p 95% one-sided lower confidence interval specificity for these tests is only 45.1%; See e.g., Toxicology in Vitro 28 (2014); 1046-1065. This indicates that 54.9% of the time, this approach predicts that a non-irritant is an irritant. This means that roughly half of the non-irritant chemicals and products tested would be misclassified as irritants using these assays. Excessive over-prediction of risk limits the utility of a test method and makes such a test less desirable to manufactures and could result in the public disregarding warning labels, thereby hindering commercialization of safe products. In addition to the high number of false positives (non-irritants classified as irritants), the Irritection/Eytex assay method also misses potentially dangerous irritants (false negatives), with an overall Mid-p 95% one-sided lower confidence interval concordance of only 68.06%. Based on accuracy data of the Irritection/Eytex method, it is clear that this test method fails to account for all relevant variables, or is otherwise confounded, and therefore fails to predict ocular irritancy with any useful degree of accuracy.

An accurate ocular irritation assay should assess chemical damage to the epithelial and endothelial cells surrounding blood vessels, in addition to opacity of the cornea while controlling for pH buffering effects. It is commonly assumed that damage to the cornea result from a variety of functional groups such as acids, bases, ketones, aldehydes, alcohols, and strong oxidants. However, it was found that measured pH effects on a water-soluble protein based test system are not predictive of irritation outside of pH extremes.

Unexpectedly, changes in pH confound the test system, and greatly reduce accuracy. Measuring pH effects induced by the test substance produces false positives and false negatives which are completely unrelated to the irritation potential of the test substance. Surprisingly, sensitivity and specificity can be greatly improved by controlling for the pH effects of the test substance by subtracting the effects induced by the pH of the test substance from the measured value for both the test substance and the standards to which it is compared.

Simple measures of pH or standard acid/alkaline reserve tests do not predict eye damage beyond the very extremes. In addition, proteins can be denatured by a variety of mechanisms, such as heat, pH extremes, oxidation, and direct reactions. A single chemical may damage macromolecules through multiple mechanisms. However, in all cases, it is commonly assumed that a macromolecule's susceptibility to damage is pH dependent; chemicals that partially unfold a macromolecule are presented with a structurally different target and therefore result in a different level of damage. It is not obvious to separate pH effects from other effects in a water-soluble system because these two effects are assumed synergistic with one another. All experts familiar with the state of the art would agree that pH measures a dominant force in protein folding/denaturation, and therefore should be included in a test that measures protein denaturation.

The mechanism responsible for the unexpected finding that measurement of pH effects confounds traditional assays is believed to relate to two stages of pH or buffering effects that occur in tissue. In the first stage, the acid or base is buffered by the test matrix, thereby maintaining pH of the test solution. As a result, the pH of the solution does not change, although denaturation may or may not occur. The second stage of pH effects is not modeled by a simple protein/glycoprotein test matrix. Living tissue has dynamic pH buffering, related to respiration and the carbonic acid/$CO_2$ equilibrium. Accordingly, in vitro test systems that do not model or control for dynamic pH buffering, over-predict the effect of pH damage/denaturation for acids and may show pH related denaturation. Therefore, it has been found that the dynamic pH buffering of the human eye must be modeled, or alternatively, measurable changes in the test matrix induced by pH effects must be subtracted because they are not representative of in vivo results.

As described above, different variables at three areas of the eye must be measured to determine if a chemical is an irritant. These areas are the cornea, conjunctiva and iris. A water phase denaturation of a protein based test substance similar to collagen is only relevant to the prediction of corneal opacity. Damage to the conjunctiva and iris results from chemicals that damage and destroy the membranes of epithelial cells and endothelial cells that surround blood vessels. Such damage results in the escape of red blood cells and damage to individual blood vessels, resulting in redness of the eye. These membrane targets are insoluble and cannot be assessed in a traditional water based test system. To accurately evaluate a substance's potential irritancy, a non-water based (hydrophobic) assay may be conducted in addition to a water phase test system, to properly characterize chemicals that exert their effect on the conjunctiva and iris. It is not currently practical or cost effective to construct a test system made solely of intact cell membranes. However, surprisingly we have found that measurable change/damage to hydrophobic organic polymers correlate with both damage to cell membranes and damage to the conjunctiva of the eye. Hydrophobic organic polymers have not been an obvious target for use as a test matrix for the prediction of irritation. Since chemicals that induce irritation damage include a range of water-soluble and water insoluble macromolecules, this second assessment can greatly increase the accuracy of the overall assay.

Disclosed herein is a combination of a water-soluble test matrix that can control for pH effects, and a water insoluble test-matrix which accurately models corneal opacity, conjunctiva redness and blood vessel damage. This test can be adapted to test a wide range of compounds including both soluble and insoluble solids, and is significantly more accurate than prior methods.

In some embodiments, the method disclosed herein proceeds by adding a test substance to an aliquot of a water-soluble protein/glycoprotein test matrix to form a test solution. The macromolecule based test matrix behaves as an active agent in the assay and is capable of undergoing a measurable change when exposed to an ocular irritant. The measurable change may be a change in appearance, which can be measured by spectrophotometry. One or more standards of known toxicity are added to at least a second aliquot of the water-soluble matrix to form control solutions, to generate a calibration curve. The measurable change induced by the test substance can be compared to the measurable change induced by the standards to make an ocular toxicity prediction. For instance, test substances that induce an equal or greater reaction than a known irritant may be classified as ocular irritants. In some embodiments, the pH of the control solution may be adjusted to match the pH of the test solution, thereby controlling for pH effects and increasing accuracy. In some embodiments, a test substance which is at least partially water insoluble is added to an aliquot of a reagent comprised of one or more hydrophobic organic polymers capable of undergoing a measurable change in response to water insoluble ocular irritants. The measurable change may be a change in appearance, which can be measured by spectrophotometry. One or more standards of known toxicity are added to at least a second aliquot of the reagent to generate a calibration curve. The measurable change induced by the test substance can be compared to the measurable change induced by the standards to make an ocular toxicity prediction in the manner described above. Water-soluble and water-insoluble assays can be performed tants (from published in vivo irritancy tests) are shown for both sub-assays. Parenthetical indicates include TP—true positive, FN—false negative, and TN—true negative (based on comparison with the in vivo test results). The results demonstrate that it is desirable to use both the water-soluble and water-insoluble sub-assays to more fully reveal irritancy potential and enhance overall accuracy.

Taken together the disclosed water-soluble and water-insoluble sub-assays provide an unexpected and surprising accuracy/concordance around 80-90% or better and can have a sensitivity of 100% (see e.g., Table 2). In one aspect, sensitivity is a more important measure because it predicts if the substance being tested is safe. However, overall accuracy is also important in making the test system useful. The methods and test matrices described herein have also been internally evaluated and evaluated by the National Toxicology Program ("NTP"—part of the National Institute of Health). The NTP is currently seeking alternatives to animal testing for routine risk assessment applications. The NTP Interagency Center for the Evaluation of Alternative Toxicological Methods ("NICEATM") provided blinded ("coded") test samples to independently evaluate the disclosed method.

TABLE 2

| N | Name | CAS # | Water soluble assay (Alpha) | water insoluble assay (Delta) | in vivo |
|---|---|---|---|---|---|
| 1 | Benzyl Alcohol | 100-51-6 | >60 (TP) | 31.1 (TP) | Category 1 |
| 2 | tetrahydrofuran | 109-99-9 | 7.67 (FN) | >60 (TP) | Category 1 |
| 3 | Cyclohexanol Isocyanate | 3173-53-3 | 9.2 (FN*) | 34.76 (TP) | Category 1 |
| 4 | 3-Methyl-1-Pentyn-3-ol | 77-75-8 | 49.56 (TP) | 0 (FN) | Category 1 |
| 5 | Pyridine | 110-86-1 | >60 (TP) | >60 (TP) | Category 1 |
| 6 | Hydroxyethyl acrylate | 818-61-1 | 25.37 (TP) | 0 (FN) | Category 1 |
| 7 | n-Octylamine | 111-86-4 | >60 (TP) | >60 (TP) | Category 1 |
| 8 | Organofunctional Silane | 82985-35-1 | 25.53 (TP) | >60 (TP) | Category 1 |
| 9 | Trichloroacetyl chloride | 76-02-8 | >60 (TP) | >60 (TP) | Category 1 |
| 10 | Diethylethanolamine | 100-37-8 | 53.54 (TP) | 0 (FN) | Category 1 |
| 11 | 2,2-Dimethyl Butanoic Acid | 595-37-9 | 38.3 (TP) | 0 (FN) | Category 1 |
| 12 | 4-(1,1,3,3-Tetramethylbutyl)phenol | 140-66-9 | >60 (TP) | 0 (FN) | Category 1 |
| 13 | 3,4-Dichlorophenyl isocyanate | 102-36-3 | >60 (TP) | 5.68 (FN) | Category 1 |
| 14 | Butyl cellosolve | 111-76-2 | 44.52 (TP | 0 (FN) | Category 1 |
| 15 | Ethyl a-hydroxyisobutyrate | 80-55-7 | >60 (TP) | 10.91 (FN*) | Category 1 |
| 16 | Methylthioglycolate | 2365-48-2 | 56.42 (TP) | 5.68 (FN) | Category 1 |
| 17 | Chloroform | 67-66-3 | 6.44 (FN) | 26.49 (TP*) | Category 1 |
| 18 | tetramethyl-1,6 hexanediame | 111-18-2 | 18.6 (TP) | 32.06 (TP) | Category 1 |
| 19 | 1-Hexanol | 111-27-3 | 26.7 (TP) | 0 (FN) | Category 2A |
| 20 | 2-Propanol | 67-63-0 | 16.46 (TP) | 0 (FN) | Category 2A |
| 21 | d-limonene | 138-86-3 | 6.37 (FN) | 27.7 (TP) | Category 2A |
| 22 | Ethyl 2-methyl | 609-14-3 | 10.9 (FN) | >60 (TP) | Category 2B |
| 23 | Ethanolamine | 141-43-5 | 52.37 (TP) | 0 (FN) | Category 2B |
| 24 | Dodecane | 112-40-3 | 6.47 (TN) | 0 (TN) | Not Classified |
| 25 | 1,6-Dibromohexane | 629-03-8 | 6.17 (TN) | 4.78 (TN) | Not Classified |
| 26 | 1-Bromo-4-chlorobutane | 6940-78-9 | 6.07 (TN) | 0.064 TN) | Not Classified |
| 27 | 2-Ethylhexyl 4-(dimethylamino)benzoate (2-Ethylhexyl p-dimethylamino benzoate) | 21245-02-3 | 6.65 (TN) | 0.97 (TN) | Not Classified | in parallel, or multiplexed, to rapidly and efficiently predict the ocular toxicity of a wide range of compounds.

In some embodiments, a membrane disc is placed between the reagent and the test substance. This allows the assay to model indirect denaturation of macromolecules across membranes within the eye. Membrane discs are commercially available. See e.g., FALCON™ cell culture inserts available from Fisher Scientific; and MILLICELL® cell culture inserts available from EMD Millipore.

Results for various known water-soluble and water-insoluble test substances are tabulated below in Table 2. The relative irritancy predictions for different categories of irri- In 2013, at the request of the test method developer, Lebrun Labs, NICEATM identified a panel of reference chemicals against which to validate the disclosed assay methods. These chemicals represented a range of physical and chemical properties and hazard classes. Lebrun Labs used the panel in coded form in a validation study. NICEATM's initial review of the validation study data indicated that the disclosed method compared favorably to other in vitro ocular toxicity testing methods.

In 2014, the Interagency Coordinating Committee on the Validation of Alternative Methods ("ICCVAM") reactivated its Ocular Toxicity Working Group to provide guidance to Lebrun Labs on additional validation activities necessary to thoroughly evaluate this test method and determine its potential regulatory utility.

Some embodiments of the disclosed assay employ preliminary analyses (pretests) to ascertain chemical and physical properties of the test substance. In some embodiments, the preliminary analyses comprise analyzing the pH of the test substance, and/or analyzing the test substance to determine if it is soluble in aqueous systems (or at least partially water-insoluble), and/or acts as a surfactant, and/or interferes with spectrophotometric analysis. Subsequent testing procedures may be adapted to more accurately assess the test substance in accordance in accordance with findings in the pretest(s).

Accordingly, by adapting the test protocol to the physical and chemical characteristics of the test substance as described above, the assay disclosed herein is able to provide more accurate predictions than assays described in the prior art.

In some embodiments related to the water-soluble subassay, the test matrix is a water-soluble active agent comprising one or more macromolecules in aqueous solution. Such a water-soluble active agent can be any mixture of water-soluble molecules and macromolecules which may comprise amino acids, peptides, proteins, lipids, glycoproteins, carbohydrates or natural or synthetic polymers. In some embodiments, the water-soluble active agent comprises at least one of isoleucine, glutamine, leucine, lysine, tyrosine, valine, proline, methione, fumerase, serine, urocanate, triacyl glycerol, globulin, gammaglobulin, mucopolysaccharide, albumin, carbohydrates, lipids, saponins, conalbumin, ovalbumin, ovomucoid, mucin, egg white fractions, plant extract, cell extract, milk fractions, red blood cell extract, muscle extract, gelatin fractions, heme, aspartate, lignocerate, stearate, linolenate, benzoate, carnitine, palmate, coenzyme A, and urea. The molecules and macromolecules can be derived as crude cell or tissue extracts, or obtained individually or in part and reconstituted.

In some embodiments related to the water-insoluble subassay, the reagent is a referred to as a water-insoluble "delta" reagent. This component is a formulation of polymers. They can be derived as crude cell or tissue extracts or obtained individually or in part and reconstituted. The resulting hydrophobic polymer matrix should demonstrate measurable optical changes when in contact with chemical toxins. In one embodiment, the hydrophobic polymer reagent has a low starting optical density (e.g., zero (0) optical density (OD) at 700 nanometers) and the optical density must increase when standards or substances to be tested are reacted with it in a reaction formulation. In some embodiments, the hydrophobic polymer is comprised of one or more organic polymers. Suitable organic polymers include polyester, polyethaline, polystyrene, polypropaline, ethyline-vinyl acetate, ester linked polymers, and ester linked lipid polymers, among others.

In some embodiments, a blanking buffer is employed to establish a background optical density or opacity of the test and control solutions. A blanking buffer may comprise a non-reactive solution such as a salt mixture. Suitable salts are not particularly limiting, and may include e.g., $CaCl_2$, KCl, $MgSO_4$, NaCl, ferric chloride, ferrous chloride, MgCl, CaCl, sodium chromate, potassium permanganate, monosodium glutamate, and $NH_4$, among others. In some embodiments, buffers are included. Suitable buffers may include $NaH_2PO_4$, HEPES, Tris, Tricine, citrate buffer, acetate buffer, CHES, MOPS, cacodylate, Bicine, and TAPS, among others. Other constituents including EDTA, N-ethylmaleimide, $NaN_3$, Glucose, fructose, and mannose, among others.

In some embodiments, a membrane disc is employed to model indirect denaturation of macromolecules across a membrane via osmotic effects, which can occur at the cornea, corneal stroma, and corneal epithelium.

In some embodiments, known irritants may include one of more of Dodecanaminium, N-(2-hydroxy-3-sulfopropyl)-N, N-dimethyl-, inner salt, 1-Naphthaleneacetic acid (solid), 1-Octanol, 1,2,4-Triazole, sodium salt, 1,3-Di-isopropylbenzene, 1,3-Diiminobenz (f)-isoindoline, 1,5-Hexadiene, 2-Benzyl-4-chlorophenol, 2-Benzyloxyethanol, 2-Ethoxyethyl acetate (Cellosolve acetate), 2-Ethyl-1-hexanol, 2-Hydroxyisobutyric acid ethylester, 2-Hydroxyisobutyric acid, 2-Methyl-1-pentanol, 2-Methylbutyric acid, 2-Naphthalenesulfonic acid, 6-hydroxy-, monosodium salt, polymer with formaldehyde and hydroxymethylbenzenesulfonic aid monosodium salt, 2-Nitro-4-thiocyanoaniline, 2,2-Dimethyl-3-pentanol, 2,2-Dimethyl butanoic acid, 2,5-Dimethyl-2,5-hexanediol, 2,6-Dichlorobenzoyl chloride, 2,6-Dichloro-5-fluoro-beta-oxo-3-pyridinepropanoate, 3-Chloropropionitrile, 3,3-Dithiodipropionic acid, 3,4-Dichlorophenyl isocyanate, 4-(1,1,3,3-Tetramethylbutyl)phenol, 4-tert-Butylcatechol (85%), 4-Carboxybenzaldehyde, 4-Chloro-methanilic acid, 6-Methyl purine, p-tert-Butylphenol, Acetic acid, Acetone, Acid blue 40, Acid red 92, alpha-Ketoglutaric acid alpha, Ammonia, Aluminum chloride, gamma-Aminopropyltriethoxy silane, Ammonium nitrate, Antimony oxide, Benzalkonium chloride, Benzalkonium chloride (10%), Benzenesulfonyl chloride, Benzethonium chloride (10%), Benzene, 1,1'-oxybis-, tetrapropylene derivatives, sulfonated, sodium salts, Benzotrichloride, Benzyl alcohol, beta-Resorcylic acid, Bis-(3-aminopropyl) tetramethyl disiloxane, Butanol, Butyl acetate, Butyl cellosolve, Butyl Dipropasol Solvent, Butylnaphthalenesulfonic acid sodium salt, Butyrolactone, Calcium thioglycolate, Captan 90-concentrate (solid), Camphene, Cetylpyridinium bromide (10%), Cetylpyridinium chloride (10%), Cetyltrimethylammonium bromide (10%), Chlorhexidine, Chloroform, Cyclohexanol, Cyclohexanone, Cyclohexyl isocyanate, Cyclopentanol, Deoxycholic acid sodium salt (10%), Di(2-Ethylhexyl) sodium sulfosuccinate (10%), Di(propylene glycol) propyl ether, Dibenzoyl-L-tartaric acid, Dibenzyl phosphate, Diethylaminopropionitrile, Diethylethanolamine (25%), Dimethyl sulfoxide, Distearyldimethylammonium chloride, Dodecane, Domiphen bromide (10%), Ethanol, Ethyl 2-methyl acetoacetate, Ethyl acetate, Ethyl trimethyl acetate, Glycidyl methacrylate, Granuform, Hexyl cinnamic aldehyde, Hydroxyethyl acrylate, Imidazole, Isobutanal, Isobutyl alcohol, Isopropyl alcohol, Lactic acid, Lauric acid, Lauryldimethylamine oxide, Lime, m-Phenylene diamine, Magnesium hydroxide, Maneb (solid), Methoxyethyl acrylate, Methyl acetate, Methyl amyl ketone, Methyl cyanoacetate, Methyl cyclopentane, Methyl ethyl ketone (2-Butanone), Methyl isobutyl ketone, Methylpentynol, Methylthioglycolate, Myristyl alcohol, n-Acetyl-methionine, n-Butanol, n-Hexanol, N-Laurylsarcosine sodium salt (10%), n-Octylamine, N,N, N',N'-Tetramethylhexanediamine, Naphthalenesulfonic acid, butyl-, polymer with formaldehyde and 2-naphthalenesulfonic acid, sodium salt, Nitric acid, Organofunctional Silane 45-49, Phosphorodichloridic acid, ethyl ester, Polyoxyethylene(10) poly oxypropylene(1.5) lauryl-myristyl ether, Polyoxyethylene(13) (mono-, di-, tri-) styrenated phenyl ether, Polyoxyethylene(19) (mono-, di-, tri-) styrenated phenyl ether, Polyoxyethylene(20) hydrogenated tallow amine, Polyoxyethylene(23) lauryl ether, Potassium laurate (10%), Potassium oleate, Promethazine hydrochloride, Potassium hydroxide, Propasol solvent P, Protectol PP, Pyridine, Quinacrine, Quaternary ammonium compounds, benzyl-C12-16-alkyldimethyl, chlorides, Quaternary ammonium compounds, di-C12-15-alkyldimethyl, chlorides, Silver nitrate, Sodium 2-naphthalenesulfonate, Sodium hydrogen difluoride, Sodium hydrogen sulfate, Sodium hydroxide (10%), Sodium lauryl sulfate, Sodium lauryl sulfate (15%), Sodium monochloroacetate, Sodium oxalate, Sodium perborate tetrahydrate, Sodium polyoxyethylene(3) lauryl ether sulfate, Sodium salicylate, Stearyltrimethylammonium chloride, Styrene, Sucrose fatty acid ester, Sulfuric acid, tetra-N-Octylammonium bromide, Tetraethylene glycol diacrylate, Tetrahydrofuran, TNO-35 (Propyl lactate), Toluene, Trichloroacetic acid (30%), Trichloroacetyl chloride, Triethanolamine, Triethanolamine polyoxyethylene (3.0) lauryl ether sulfate, Triton X-100, Triton X-100 (5%), Triton X-100 (10%), Tween 20, Xylene, and Zinc chloride.

In some embodiments, known non-irritants may include one or more of 1-Bromo-4-chlorobutane, 1-Methylpropyl benzene, 1,3-Di-isopropylbenzene, 1,9-Decadiene, 2-Ethylhexyl p-dimethylamino benzoate, 2-Methylpentane, 2-(n-Dodecylthio)ethanol, 2,2-Dimethyl-3-pentanol, 2,4-Difluoronitrobenzene, 2,4-Pentanediol, 3-Methoxy-1,2-propanediol, 3-Methylhexane, 3,3-Dimethylpentane, Acrylic acid homopolymer sodium salt, Di-n-propyl disulphide, Diisobutyl ketone, Ethylhexyl salicylate, Glycerol, Iso-octyl acrylate, Isopropyl bromide, Isopropyl myristate, iso-Octylthioglycolate, Methyl trimethyl acetate, n-Hexyl bromide, n-Octyl bromide, n,n-Dimethylguanidine sulfate, Polyethylene glycol 400, Polyethyleneglycol monolaurate (10 E.O.), Polyoxyethylene hydrogenated castor oil (60E.O.), Polyoxyethylene(14) tribenzylated phenyl ether, Polyoxyethylene(160) sorbitan triisostearate, Polyoxyethylene(40) hydrogenated castor oil, Potassium tetrafluoroborate, Propylene glycol, Sodium lauryl sulfate (3%), Sorbitan monolaurate, tetra-Aminopyrimidine sulfate, Toluene, Triton X-100 (1%), and Tween 80.

As used herein, "toxicity" is used to refer to a substance's ability to damage, irritate, or otherwise negatively affect an eye. Toxicity may be evidenced by pain, irritation, swelling opaqueness, redness, and discharge. Such effects may be temporary or permanent. Accordingly, the word "toxicity" is defined broadly to include any discomfort or disfavorable experience associated with the presence of a substance contacting an eye. As used herein, "irritancy" or "irritant" is used broadly to cover the spectrum of between non-irritating (non-toxic) to highly corrosive.

EXAMPLES

The following Examples are presented for the purposes of illustration and should not be construed as limitations.

Example 1

Verification of Accuracy

Over Gold Standard, chemicals were used to develop and internally validate this approach. NICEATM is a division of the National Toxicology Program (NTP) mandated by the U.S. government to evaluate alternative methods intended to reduce, refine and replace animal testing within the United States.

Using the procedure described below, a blind sample of compounds was assayed, and the following results were obtained. The results were sent to NICEATM. NICEATM performed an analysis on the data and reported the following accuracies:

Below is the NICEATM Data:
For the EPA Classification System:
Cut Off A
Accuracy=92%
Sensitivity=93%
Specificity=92%
For the GHS Classification System:
Accuracy=88%
Sensitivity=89%
Specificity=86%

Notably, the EPA and GHS systems are not harmonized. Arguably, the GHS system is the dominant system in the EU and the EPA system is desirable in the US. It has been reported that animals only predict human irritancy with an accuracy of 80%. These accuracy statistics indicate that this approach is more useful, more humane, and accurate than prior methods, including in vivo animal testing.

Example 2

Pretest

A first pretest is performed to determine if the test substance is soluble in the blanking buffer. 200 µL of test sample is mixed with 2 mL of blanking buffer, and visually analyzed to determine if the substance has mixed. If the substance does not mix, it is allowed to rest for 30 minutes. A sample of the solution is then removed, and the absorbance of the sample at 400 nm ($OD_{400}$) is measured. If the $OD_{400}$ is less than 0.100, then the substance is classified as completely insoluble. If the $OD_{400}$ is greater than 0.850, then the substance is classified as intensely colored and must be analyzed at an alternate wavelength.

A second pretest is performed to determine if the test substance is a surfactant. A sample of test substance is mixed with blanking buffer, and vortexed for ten seconds. The mixture is allowed to rest for five minutes, and is then inspected for froth. If froth extends greater than 0.2 cm above the meniscus, then the substance is classified as a surfactant.

A third pretest is performed to measure the buffering power of the unknown test substance. Active agent is procured, its pH is adjusted to 6.36, and 1.25 mL is added to a test tube. Next, 125 µL or mg of test substance is added to the test tube. The pH of the mixture is recorded. The final pH is compared to the starting pH and the absolute value of the change in pH is applied as an exponent to base 10 to generate a buffering score. These pretest results are used to select specific procedures to further analyze the test substance. Compounds with a buffering score between 5 and 2 are within the MA α domain. Compounds outside of the MA α domain with buffering scores less than 100 are within the HMA α domain. Substances with a buffering score of at least 100 are within the H-test domain.

Example 3

MA α Procedure

The MA α procedure is used to test unknowns that have a small buffering capacity. The MA α procedure predicts a substance's capacity for indirect denaturation of molecules across a membrane via osmotic effects, such as osmotic effects across the corneal epithelium and stroma which can damage the cornea. The MA α assay further analyzes Potential to damage tissue via excessive oxidation and reactivity, which can occur at the epithelium, stroma, conjunctiva and iris. Finally, the MA α assay analyzes direct denaturation of macromolecules that model ordered collagen, which can occur at the corneal stroma. The MA α assay proceeds as follows.

Figure 2A:
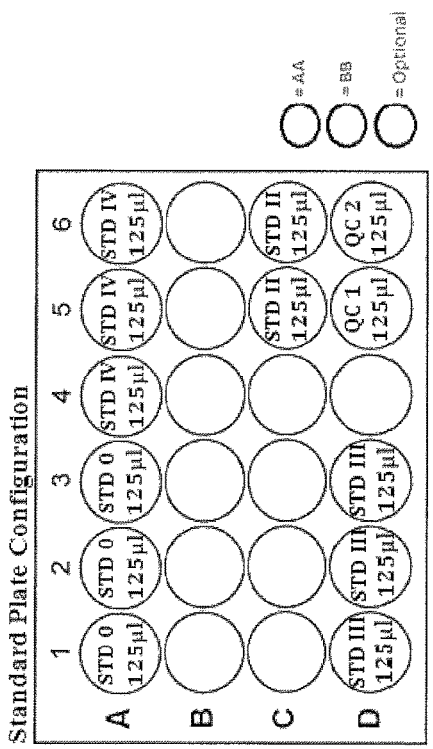
FIGS. 2A-B shows example plate configurations to perform a membrane analysis.
Figure 2B:
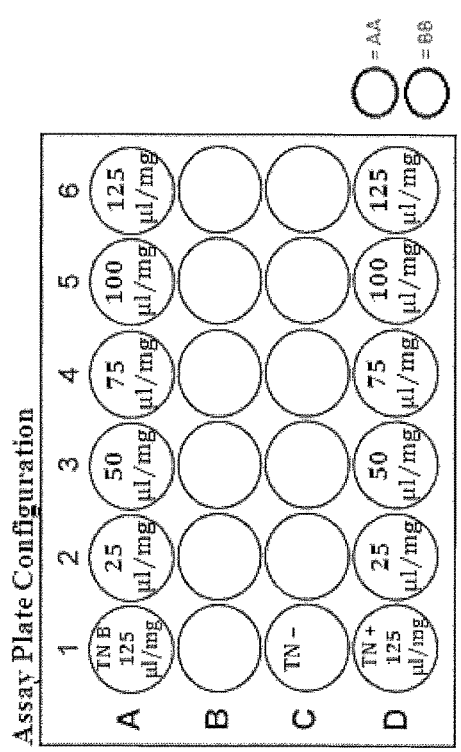
Figure 3A:
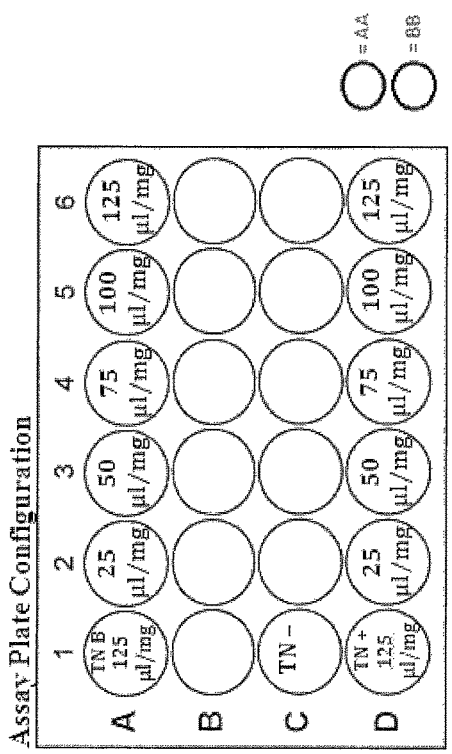
FIGS. 3A-B show example plate configurations to perform an alternative membrane analysis.

Active agent is procured, and its pH is adjusted to 6.36. Two sets of plates are arranged according to FIGS. 2A and B. 1.25 mL of active agent and 1.25 mL of blanking buffer are added to the indicated wells. A membrane disc is then placed atop the active agent and blanking buffer solution. Next, 125 µL of Standards are added to the indicated wells. Indicated amounts of unknown test sample are also added to the wells shown in FIG. 3A. Finally, 125 µL of TNI and TNII solution is added to the indicated wells.

The plates are then incubated for 17.5-18.5 hours at 30.6-31.0 C. After incubation, the plate is removed from the incubator. The membrane disc is removed from the plate and inspected for damage. The solution remaining in each well is then mixed, and the $OD_{400}$ is measured.

The $OD_{400}$ values corresponding to the test substance are compared to the $OD_{400}$ values of the standards, and an optical toxicity prediction is made by identifying the standard with the closest $OD_{400}$ value.

Calculations

Sample OD values are recorded. Blank OD values are recorded. Standard 0 values are recorded and averaged. Each Standard's Values (e.g., Standard IV, Standard III, etc.) are recorded.

Blank OD values and the average standard 0 values are subtracted from the Sample values to determine the Measured Value. For example, Measured Value=Sample Value−(Blank OD Value+ Average Standard 0 Value)

Each Standard has a Standard Value calculated by subtracting the Average Standard 0 Value from the recorded Standard Value for that standard. For example, Standard Value IV=Recorded Standard Value IV−Average Standard 0

For each Measured Value, a numerical score is assigned by identifying the closest calculated Standard Value (e.g., Standard Value IV), and then dividing the Measured Value by the closest calculated Standard Value. Finally, a multiplier is applied to the quotient based on the closest Standard Value's designation according to the table below.

| Standard Value | Multiplier |
| --- | --- |
| I | 60 |
| II | 30 |
| III | 12.5 |
| IV | 8 |

A True Negative 1 Value is calculated. The OD value of the well containing blanking buffer and 125 µL of test substance and the OD value of the TN 1− well are subtracted from the OD of the TN1+ OD. If the True Negative 1 value is less than the negative value of the Standard 0 measured value, then the substance is considered an irritant, and an irritation score is calculated by identifying the closest standard value, dividing the measured value by the closest standard value, and applying a multiplier based on the Standard Value table above. A True Negative II Value is calculated in the same manner.

The calculated irritation score is converted into EPA and GHS categories using the tables below.

Non-Irritant Versus the Rest Prediction Models:
EPA 2-Category Prediction Model

| Irritation Score | EPA Classification |
| --- | --- |
| 0-8.0 | Category IV |
| >8.0 | Category III or II or I |

GHS 2-Category Prediction Model

| Irritation Score | GHS Classification |
| --- | --- |
| 0-12.5 | NC |
| >12.5 | Category 2 or 1 |

Multiple Category Prediction Models:
MAα EPA Prediction Model

| Irritation Score | EPA Classification |
| --- | --- |
| 0-8.0 | Category IV |
| >8.0-12.5 | Category III |
| >12.5-65.0 | Category II |
| >65.0 | Category I |

MAα GHS Prediction Model

| Irritation Score | GHS Classification |
| --- | --- |
| <12.5 (*14) | NC |
| >12.5-41.0.0 | Category $2_{(High\ Sensitivity)}$ |
| >14.0-65.0 | Category $2_{(High\ Specificity)}$ |
| >65.0 | Category $1_{(High\ Specificity)}$ |

A substance is considered positive if any dose exceeds the EPA or GHS cutoff. The highest irritation score is used.

Example 4

AMA α Procedure

The HMA α procedure is used to test unknowns that have a medium buffering capacity. The HMA α procedure predicts a substance's capacity for indirect denaturation of molecules across a membrane via osmotic effects, such as osmotic effects across the corneal epithelium and stroma which can damage the cornea. The HMA α assay controls for pH effects and further analyzes potential to damage tissue via excessive oxidation and reactivity, which can occur at the epithelium, stroma, conjunctiva and iris. Finally, the HMA α assay analyzes direct denaturation of macromolecules that model ordered collagen, which can occur at the corneal stroma. The MA α assay proceeds as follows.

Active agent is procured, and its pH is adjusted to 6.36. A series of five test tubes is prepared by adding 1.25 mL of active agent into each test tube, and then adding 25 µL of sample to the first tube, 50 µL of sample to the second tube, 75 µL of sample to the third tube, 100 µL of sample to the fourth tube, and 125 µL of sample to the fifth tube. The pH of each tube is measured and recorded.

Figure 3B:
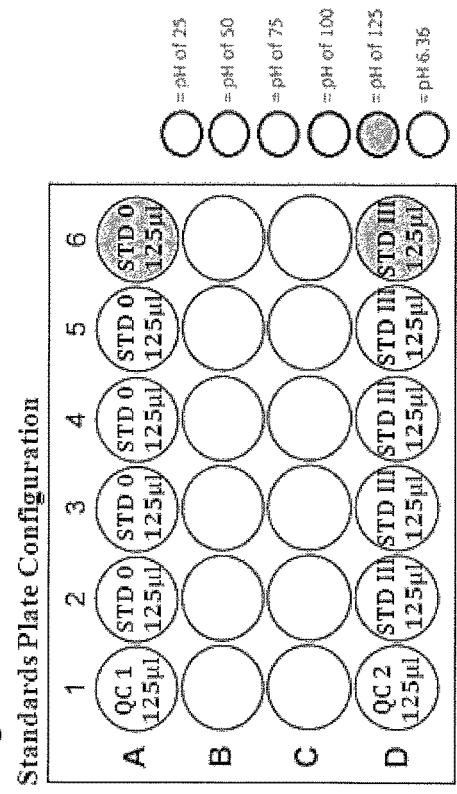

A new portion of active agent is procured, and its pH is adjusted to each measured value. When each measured value is achieved, 1.25 mL of active agent is added into the two wells indicated in FIG. 3B. When the pH reaches 6.36, aliquot 1.25 mL of active agent into the nine wells indicated in FIG. 3B. Additional 1.25 mL portions of active agent are added into any other plates that will be used for other assays. Finally, 1.25 mL of blanking buffer is added into each indicated well. If the pH achieved by the test substance in active agent is lower than 6.36, the pH of the active agent must be lowered to the same pH before active agent is aliquoted into any standards plates.

Once the wells are filled, a membrane disc is placed into each well. Next, Standards, QC1 and QC2 are added within the membrane discs in the indicated wells in FIG. 3B. Finally, the indicated amount of test substance is added to the wells indicated in FIG. 3A. 125 µL of TNI and TNII solution is added to the wells indicated in FIG. 3B. Five replicates of standard 0 and five replicates of standard III are added to the active agent pH titration corresponding to the pH achieved by adding test substance to active agent.

The plates are then incubated for 17.5-18.5 hours at 30.6-31.0 C. After incubation, the plate is removed from the incubator. The membrane disc is removed from the plate and inspected for damage. The solution remaining in each well is then mixed, and the $OD_{400}$ is measured.

The $OD_{400}$ values corresponding to the test substance are compared to the $OD_{400}$ values of the standards, and an optical toxicity prediction is made by identifying the standard with the closest $OD_{400}$ value.

Calculations

Sample OD values are recorded. Blank OD values are recorded. Measured values are calculated by subtracting the blank OD value and the standard 0 OD value with the corresponding pH from the Sample OD value for reach respective concentration.

Measured Value=Sample OD−(Blank+Standard 0 with corresponding pH)

A Standard Value is obtained by subtracting the average standard 0 value with the corresponding pH from the measured value.

For each of the measured unknown test values, a numerical score is assigned by using Standard III.

The measured OD is divided by the standard value with the corresponding pH. A multiplier is applied to this quotient based on the designation of the standard according to the table below.

| Standard Designation | Multiplier |
| --- | --- |
| III | 12.5 |
| IV | 8.0 |

The resulting value is the irritation score for the corresponding sample.

A TNI value is calculated by subtracting the TNIB and the TNI− ODs from the TNI+ OD. The irritation score for TNI is calculated according to the steps above. A TNII score is calculated in the same manner.

The highest irritation score is used, and a classification prediction is made based on the tables below.

Non-Irritant Versus the Rest Prediction Models:
AMA EPA 2-Category Prediction Model

| Irritation Score | EPA Classification |
| --- | --- |
| 0-7.0 | Category IV |
| >7.0 | Category III or II or I |

AMA GHS 2-Category Prediction Model

| Irritation Score | GHS Classification |
| --- | --- |
| 0-12.5 | NC |
| >12.5 | Category 2 or 1 |

Multiple Category Prediction Models:
AMAα EPA Prediction Model

| Irritation Score | EPA Classification |
| --- | --- |
| 0-7.0 | Category IV |
| >7.0-10.0$_{(if\ basic)}$ | Category III |
| >7.0-14$_{(if\ acidic)}$ | |
| >10.0-20$_{(if\ basic)}$ | Category II |
| >14-75.0$_{(if\ acidic)}$ | |
| >20.0$_{(if\ basic)}$ | Category I |
| >75.0$_{(if\ acidic)}$ | |

AMAα GHS Prediction Model

| Irritation Score | GHS Classification |
| --- | --- |
| 0-10.0 | NC |
| >10.0-20.0$_{(if\ basic)}$ | Category 2 |
| >10.0-75.0$_{(if\ acidic)}$ | |
| >20.0$_{(if\ basic)}$ | Category 1 |
| >75.0$_{(if\ acidic)}$ | |

Example 5

Completely Insoluble Procedure

The Completely Insoluble procedure is used to test unknowns that are completely insoluble in the blanking buffer. The Completely Insoluble proceeds as follows.

Figure 4A:
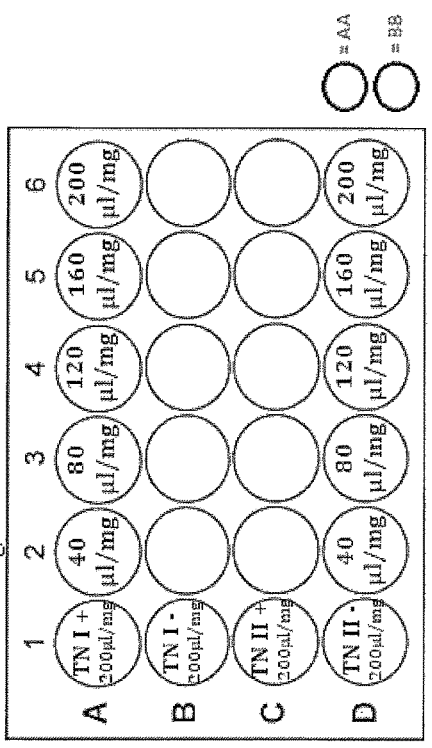
FIGS. 4A-B show example assay plate configurations to perform a completely insoluble analysis.

40, 80, 120, 160, 200 µL (or mg if solid) of unknown test sample is added directly into the wells of the assay plate as shown in FIG. 4A. For solid compounds, 1 µL is considered equivalent to 1 mg. 200 µl (or mg if solid) of test sample is pipetted into the wells of the 24 well plate labeled for TNI+ and TNII+ in FIG. 4A.

Figure 4B:
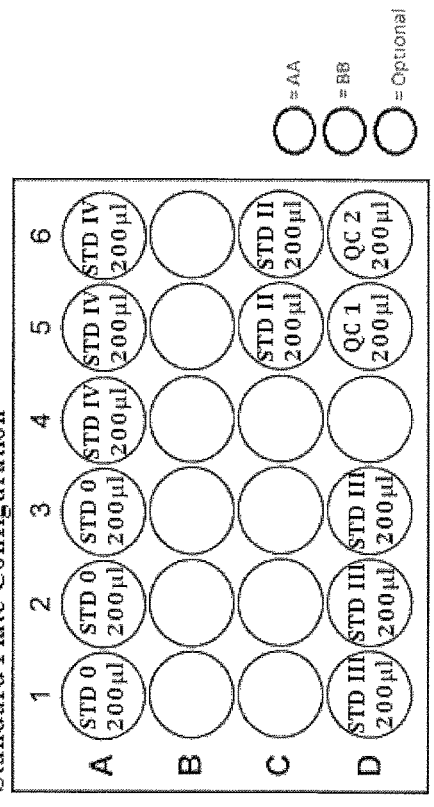

Active agent is procured, and its pH is adjusted to 6.36. 1.25 mL of active agent and 1.25 mL of blanking buffer are added to the wells indicated in FIGS. 4A-B. 2 mL of blanking solution and 2 mL of active agent is pipetted into the wells indicated in FIGS. 4A-B. Finally, 200 µL of QC1, QC2, TNI, and TNII are added to the wells indicated in FIGS. 4A-B.

Standards, QC 1 and QC 2 are added directly into the wells of the 24-well standards plate as indicated in FIG. 4B. 200 µL triplicates of standard 0 are pipetted into three wells, triplicate standard IV into three wells, and singles of Standard III and QC 1 and QC 2 into the wells indicated in FIG. 4B.

The plates are then incubated for 41.5-42.5 hours at 30.5-31.0 C. After incubation, the plate is removed from the incubator. The solution remaining in each well is then mixed, and the $OD_{400}$ is measured.

The $OD_{400}$ values corresponding to the test substance are compared to the $OD_{400}$ values of the standards, and an optical toxicity prediction is made by identifying the standard with the closest $OD_{400}$ value.

Calculations

Calculations are performed in accordance with the procedure outlined in Example 3. The highest irritation score is used and a toxicity prediction is made according to the tables below.

Non-Irritant Versus the Rest Prediction Models:
EPA 2-Category Prediction Model

| Irritation Score | EPA Classification |
| --- | --- |
| 0-7.5 | Category IV |
| >7.5 | Category III or II or I |

GHS 2-Category Prediction Model

| Irritation Score | GHS Classification |
| --- | --- |
| 0-10.0 | NC |
| >10.0 | Category 2 or 1 |

Multiple Category Prediction Models:
Ci α EPA Prediction Model

| Irritation Score | EPA Classification |
| --- | --- |
| 0-7.5 | Category IV |
| >7.5-10.0 | Category III |
| >10.0-75.0 | Category II |
| >75.0 | Category I |

Ci α GHS Prediction Model

| Irritation Score | GHS Classification |
| --- | --- |
| 0-10.0 (*14) | NC |
| >10.0-75.0 | Category 2$_{(High\ Sensitivity)}$ |
| >14.0-75.0 | Category 2$_{(High\ Specificity)}$ |
| >75.0 | Category 1$_{(High\ Sensitivity)}$ |

*For high specificity prediction

Figure 5A:
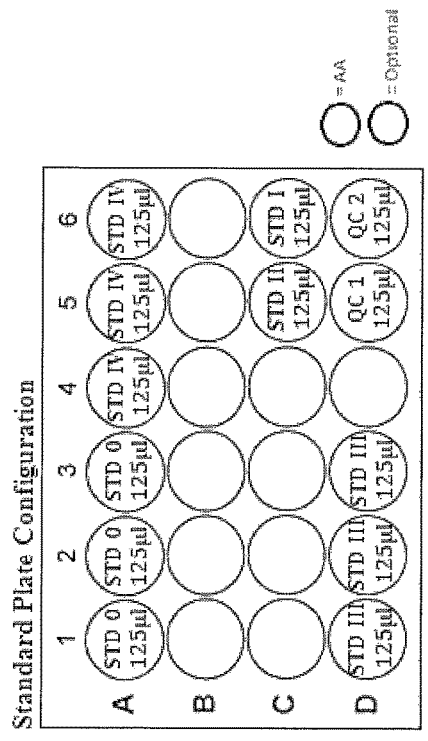
FIGS. 5A-B shows example assay plate configurations to perform an alternate completely insoluble analysis.
Figure 5B:
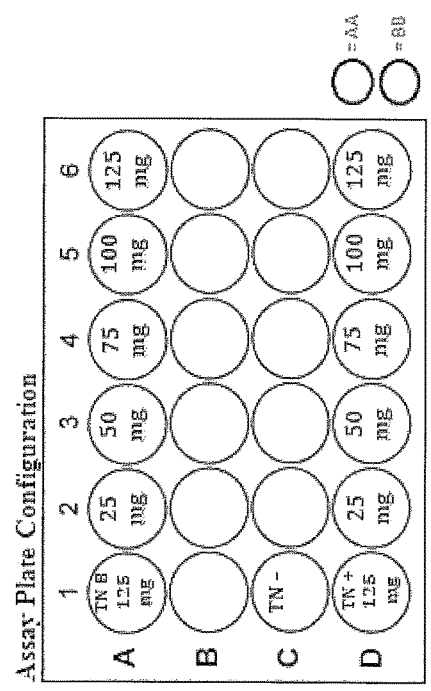

An alternate procedure may be used for completely insoluble solids that sink to the bottom of the plate. Active agent is procured, and its pH is lowered to 6.36. 1.25 mL of blinking buffer and active agent are added to the wells indicated in FIGS. 5A and B. Membrane discs are added to each standard, and QC plate, indicated in FIG. 5A. 125 µL of appropriate standard is added to each well indicated in FIG. 5A. Solid test substance is weighed, and added to each appropriate membrane disc before the disc is inserted in the wells indicated in FIG. 5B. 125 µL of TN solution is added to the discs labeled TN+, TN− and TNB in FIG. 5B. The wells are incubated, and analyzed in accordance with the procedure above.

Example 6

Δ Test Procedure

Triplicate Δ Test and Δ Control cells are labeled as follows: Test Cell 40 µL; Control Cell 40 µL; Test Cell Standard A; Test Cell Standard B. The cells are placed in a rack. 40 µL aliquots of test sample are added to the three Δ positive cells. 40 µL of Standard A+ and 40 µL of Standard B+ are added to the respective triplicate cells. 40 µL of test substance is aliquoted to the True Negative cell. All test and standard cells (A+, B+, and control cells) are filled with 2 mL of Δ reagent. The cells are capped and incubated at 30.5 to 31.3° C. for 18 to 20 hours. 2 mL of Δ reagent is added to a naïve Δ test cell to blank a spectrophotometer. The $OD_{700}$ value is measured for all test and standard cells.

Where the substance is colored or opaque, 2 mL of Δ reagent are added to a naïve control Δ cell, and the $OD_{700}$ value is measured for all control cells.

Calculations

Test Cell values are recorded. Control cell values are recorded. Where samples are colored or opaque Net $OD_{700}$ values are obtained by subtracting the average of the control cell OD700 value from the average of the test cell OD700 value. The average of positive controls A+ and B+ are calculated.

For each unknown, an irritancy classification is ascertained by using the closest positive cell value. The highest measured value is used. The standard with the closest OD value is identified as the Closest Standard Value. The Measured Value is divided by the mean of the three Closest Standard Values. A multiplier is applied to the quotient corresponding to the designation of the Closest Standard Value. If the Closest Standard Value is A+, the multiplier is 8. If the Closest Standard Value is B+, the multiplier is 12.5. The resulting value is the irritation score for the sample. The highest score is used to predict the irritancy of the sample.

The irritation score is used to make an irritancy prediction according to the tables below.

Non-Irritant Versus the Rest Prediction Models:
EPA 2-Category Prediction Model

| Irritation Score | EPA Classification |
| --- | --- |
| 0-8.0 | Category IV |
| >8.0 | Category III or II or I |

GHS 2-Category Prediction Model

| Irritation Score | GHS Classification |
| --- | --- |
| 0-12.5 | NC |
| >12.5 | Category 2 or 1 |

Multiple Category Prediction Models:
Δ EPA/GHS Prediction Model

| Criteria | EPA Prediction | GHS Prediction |
| --- | --- | --- |
| <average of Positive Standard A+ (40 µl) | Non-irritant | Non-Irritant |
| ≥average of Positive Standard A+ (40 µl) | Category III | No Prediction or Category 3 |
| ≥average of Positive Standard B+ (40 µl) | Category II or I | Category 2 or 1 |

Example 7

Procedure H

Five tubes are labeled 2%, 4%, 6%, 8% and 10%. Active agent is obtained, the pH is adjusted to 7.4, and 1.25 ml is added into each tube. The following amounts of unknown test substance are added to the appropriate tubes: 0 (control), 25 µL, 50 µL, 75 µL, 100 µL, and 125 µL (or mg if solid). Each tube is vortexed for 5 seconds, then incubated for 15-20 minutes at room temperature. After incubation, the pH of each tube is measured and recorded.

Calculations

The pH value is recorded for each dose (2%, 4%, 6%, 8% and 10%). The recorded pH is subtracted from the starting pH. The absolute value of the resulting number is applied as an exponent to base 10 to calculate the H Score. The measured H scores are converted into H Class Predictions and EPA and GHS scores/predictions using the prediction models in the table below.

Non-Irritant Versus the Rest Prediction Models:
EPA 2-Category Prediction Model

| Irritation Score | EPA Classification |
|---|---|
| 0-500 | Category IV |
| >500 | Category III or II or I |

GHS 2-Category Prediction Model

| Irritation Score | GHS Classification |
|---|---|
| 0-500 | NC |
| >500 | Category 2 or 1 |

Multiple Category Prediction Models:
H Prediction Model

| H Score | H Class | EPA Prediction | GHS Prediction |
|---|---|---|---|
| <100 | No Prediction | No Prediction | No Prediction |
| 100-500 | Likely Irritant | Needs Confirmation | Needs Confirmation |
| 500-1,000 | Irritant | III, II or I | 2b, 2a or 1 |
| >1,000 | Irritant/Corrosive | III, II or I | 2b, 2a or 1 |

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

What is claimed is:

1. An in vitro method for predicting a relative irritancy of a test substance, which is at least partially insoluble in an aqueous solution, the method comprising:
   adding the test substance to an aliquot of a hydrophobic organic polymer to form a test hydrophobic organic polymer;
   adding a known irritant to another aliquot of the hydrophobic organic polymer to form a control hydrophobic organic polymer;
   measuring an optical response of the test and control hydrophobic organic polymers after a time period; and
   predicting the relative irritancy of the test substance by comparing the measured optical response in the test and control hydrophobic organic polymers.

2. The in vitro method of claim 1, further comprising a solubility pretest for determining if the test substance is at least partially insoluble in an aqueous solution.

3. The in vitro method of claim 2, wherein the solubility pretest comprises:
   adding the test substance to an aqueous solution to form a pretest solution;
   mixing the pretest solution; and
   measuring an optical response, wherein an optical response of greater than a predetermined threshold indicates that the test substance is at least partially insoluble in an aqueous solution.

4. The in vitro method of claim 1, wherein measuring the optical response comprises measuring spectrophotometric changes in optical density, opacity or turbidity.

5. The in vitro method of claim 1, further comprising classifying the test substance as an irritant if the measured optical response produced by the test substance is greater than or equal to the measured optical response produced by the known irritant.

6. The in vitro method of claim 1, further comprising adding a known non-irritant to another aliquot of the hydrophobic organic polymer.

7. The in vitro method of claim 6, wherein more than one known irritants and/or known non-irritants are used to generate a standard curve of relative irritancy versus the measured optical response.

8. The in vitro method of claim 1, wherein the hydrophobic organic polymer comprises a polymerized hydrocarbon.

9. An in vitro method for predicting a relative irritancy of a test substance, the method comprising:
   measuring an initial pH of an aqueous solution comprising one or more macromolecules;
   adding a test substance to the aqueous solution to form a test solution;
   monitoring a shift in pH of the test solution from the initial pH to a final pH;
   adjusting the pH of aliquot of the aqueous solution comprising one or more macromolecules to the final pH using an acid or a base to form a control solution;
   adding a known irritant to a first aliquot of the control solution at the final pH;
   measuring an optical response of the macromolecules in the test solution and the control solution; and
   predicting the relative irritancy of the test substance by comparing the measured optical response in the test and control solutions.

10. The in vitro method of claim 9, further comprising adding a known non-irritant to a second aliquot of the control solution at the final pH.

11. The in vitro method of claim 9, further comprising classifying the test substance as an irritant if the optical response produced by the test substance is greater than or equal to the optical response produced by the known irritant.

12. The in vitro method of claim 9, wherein measuring the optical response comprises measuring spectrophotometric changes in optical density, opacity or turbidity.

13. The in vitro method of claim 9, wherein more than one known irritants and/or known non-irritants are used to generate a standard curve of relative irritancy versus the measured optical response.

14. The in vitro method of claim 9, wherein a background optical response is measured in the aqueous solution comprising the test substance and/or the known irritant, wherein the one or more macromolecules are not included in the aqueous solution, and wherein the background optical response is subtracted from the measured optical response in the test solution and/or control solution.

15. The in vitro method of claim 9, wherein the test substance is partially solubilized with a solvent before adding it to the aqueous solution, and wherein the optical response produced by the solvent in the aqueous solution is subtracted from the optical response produced by the test substance and the solvent.

16. An in vitro method for predicting a relative irritancy of a test substance, the method comprising:
   conducting a first assay for water insoluble irritants, the first assay comprising:
      adding the test substance to an aliquot of a hydrophobic organic polymer to form a test hydrophobic organic polymer;
      adding a known irritant to another aliquot of the hydrophobic organic polymer to form a control hydrophobic organic polymer;
      measuring an optical response of the test and control hydrophobic organic polymers after a time period; and
      predicting the relative irritancy of the test substance under hydrophobic conditions by comparing the measured optical response in the test and control hydrophobic organic polymers;
   conducting a second assay for water soluble irritants, the second assay comprising:
      adding the test substance to an aliquot of an aqueous solution comprising one or more macromolecules to form a test solution;
      adding a known irritant to another aliquot of the aqueous solution comprising one or more macromolecules to form a control solution;
      measuring an optical response of the macromolecules in the test solution and the control solution; and
      predicting the relative irritancy of the test substance under aqueous conditions by comparing the measured optical response in the test and control solutions; and
   combining the predicted relative irritancy results from the first and second assays.

17. The in vitro method of claim 16, further comprising a solubility pretest for determining if the test substance is at least partially insoluble in water.

18. The in vitro method of claim 17, wherein the solubility pretest comprises:
   adding the test substance to an aqueous solution to form a pretest solution;
   mixing the pretest solution; and
   measuring an optical response, wherein an optical response of greater than a predetermined threshold indicates that the test substance is at least partially insoluble in water.

19. The in vitro method of claim 16, wherein measuring the optical response comprises measuring spectrophotometric changes in optical density, opacity or turbidity.

20. The in vitro method of claim 16, wherein more than one known irritants and/or known non-irritants are used to generate a standard curve of relative irritancy versus the measured optical response.

* * * * *